(12) United States Patent
Drouillard et al.

(10) Patent No.: US 8,828,421 B2
(45) Date of Patent: Sep. 9, 2014

(54) METHOD FOR ENCAPSULATION OF ORALLY INGESTED MATERIALS TO ALTER THE SITE OF DIGESTION, SITE OF ACTION, OR STABILITY

(75) Inventors: James S. Drouillard, Olsburg, KS (US); Thomas J. Herald, Manhattan, KS (US); Matthew Greenquist, Holdredge, NE (US)

(73) Assignee: Kansas State University Research Foundation, Manhattan, KS (US)

( * ) Notice: Subject to any disclaimer, the term of this patent is extended or adjusted under 35 U.S.C. 154(b) by 79 days.

(21) Appl. No.: 12/967,832

(22) Filed: Dec. 14, 2010

(65) Prior Publication Data

US 2011/0081414 A1    Apr. 7, 2011

Related U.S. Application Data

(63) Continuation of application No. 10/599,618, filed as application No. PCT/US2005/011898 on Apr. 6, 2005, now abandoned.

(60) Provisional application No. 60/559,779, filed on Apr. 6, 2004.

(51) Int. Cl.
| | |
|---|---|
| A23K 1/18 | (2006.01) |
| A23K 1/16 | (2006.01) |
| A23K 1/00 | (2006.01) |
| A23L 1/00 | (2006.01) |
| A61K 9/16 | (2006.01) |
| A61K 9/50 | (2006.01) |

(52) U.S. Cl.
CPC .............. *A23L 1/0029* (2013.01); *A23K 1/1813* (2013.01); *A23V 2002/00* (2013.01); *A23K 1/1631* (2013.01); *A23K 1/005* (2013.01); *A61K 9/1658* (2013.01); *A61K 9/5052* (2013.01)
USPC .......................................................... 424/438

(58) Field of Classification Search
None
See application file for complete search history.

(56) References Cited

U.S. PATENT DOCUMENTS

| | | | | |
|---|---|---|---|---|
| 3,314,800 | A | * | 4/1967 | Noznick et al. ................. 426/93 |
| 3,962,416 | A | * | 6/1976 | Katzen ......................... 424/493 |
| 4,217,370 | A | | 8/1980 | Rawlings et al. |
| 5,360,614 | A | * | 11/1994 | Fox et al. ...................... 424/439 |
| 5,738,805 | A | * | 4/1998 | Chaundy et al. ................ 516/77 |
| 2002/0132756 | A1 | | 9/2002 | Lee |

OTHER PUBLICATIONS

Lee et al. Protein Solubility Characteristics of Commercial Soy Protein Products, Jan. 2003, JAOCS vol. 80, pp. 85-90.*
WHFoods: Peanuts (In depth nutrient analysis) accessed online on Jan. 10, 2012 at http://www.whfoods.com/genpage.php?tname=nutrientprofile&dbid=114.*
WHFoods: Peanuts (In depth nutrient analysis) accessed online on Jan. 10, 2012 at http://www.whfoods.com/genpage.php?tname=nutrientprofile&dbid= 114.*
Office Action dated Oct. 28, 2010 for EP Application No. 05 732 178.8; filed Apr. 6, 2005; Inventor: James S. Drouillard (8 pages).
XP002606498: Studies on the pH value of abomasal contents in dairy cows during the first 3 weeks after calving, Van Winden et al., J. Vet, Med. A 49, 157-160 (2002) (.

* cited by examiner

*Primary Examiner* — Johann R Richter
*Assistant Examiner* — Casey Hagopian
(74) *Attorney, Agent, or Firm* — Hovey Williams LLP

(57) ABSTRACT

Comestible materials encapsulated by a film-forming composition including a plant protein source and methods of forming the same are provided. The film-forming composition affects the site of digestion of the comestible material within the digestive tract of an animal or a human thereby allowing the material to be most effectively utilized by the body. Also, the film-forming compositions may be used to enhance the stability of the encapsulated material and prevent undesired interaction with other components of a mixture.

16 Claims, No Drawings

US 8,828,421 B2

METHOD FOR ENCAPSULATION OF ORALLY INGESTED MATERIALS TO ALTER THE SITE OF DIGESTION, SITE OF ACTION, OR STABILITY

RELATED APPLICATION

This application is a continuation of U.S. application Ser. No. 10/599,618, filed Oct. 3, 2006, entitled METHOD FOR ENCAPSULATION OF ORALLY INGESTED MATERIALS TO ALTER THE SITE OF DIGESTION, SITE OF ACTION, OR STABILITY, which is a national stage submission under 35 U.S.C. 371 of International Application Ser. No. PCT/US05/11898, filed Apr. 6, 2005, which claims the benefit of U.S. Provisional Application Ser. No. 60/559,779, filed Apr. 6, 2004. All of the foregoing applications are hereby incorporated by reference in their entireties.

BACKGROUND OF THE INVENTION

1. Field of the Invention

The present invention is directed toward protein-based films for forming encapsulated comestible materials, methods of forming encapsulated materials, and methods of feeding animals or humans with the encapsulated materials. Specifically, the protein-based films are derived from plant sources and allow the encapsulated materials to resist immediate microbial digestion in the stomach of the animal or human thereby facilitating delivery of the comestible material to a lower portion of the digestive tract.

2. Description of the Prior Art

It has been discovered that the efficacy or potency of orally ingested materials such as nutrients, supplements, and pharmaceuticals can be increased if they can be delivered to specific sites along the digestive tract of an animal or human. For example, certain nutrients are most effective when digestion occurs in the intestines as opposed to the forestomach of a ruminant animal. Various delivery systems have been proposed to delay the onset of digestion until the material reaches a specific site in the digestive tract. One such method has been to coat the material with a synthetic polymer coating. These coating materials have the drawback in that they are often not economically viable for use with certain kinds of comestible materials.

Another method has employed animal derived coating materials such as gelatin or blood meal to alter the digestive site of the encapsulated material. Currently, many vitamins are stabilized using gelatin beadlets. However, incidents involving the discovery of Bovine Spongiform Encephalopathy (BSE or "mad cow disease") in cattle populations in Europe, Asia, and Canada have led to concern over the use of gelatin (a ruminant-derived protein) in human food and animal feed products.

There exists a need for a cost effective alternative to the use of gelatin or animal derived materials to stabilize comestible particles' as to alter their site of digestion in an animal or human.

SUMMARY OF THE INVENTION

The present invention overcomes the above problems by providing an economical alternative to the use of coating materials that include animal by-products or animal-derived materials.

In one aspect, the present invention pertains to an encapsulated comestible material comprising, consisting of, or consisting essentially of at least one comestible particulate material and a coating composition applied to and encapsulating the at least one particulate material, the coating material comprising a plant-derived protein source.

In another aspect, the present invention pertains to a method of forming an encapsulated material comprising, consisting of, or consisting essentially of the steps of providing a film-forming solution comprising a plant-derived protein source, coating at least one particulate comestible material with the film-forming solution, and drying the film-forming solution on the at least one particulate comestible material thereby forming the encapsulated material.

In yet another aspect, the present invention pertains a method of feeding an animal or human comprising feeding the animal or human a particulate material encapsulated with a film-forming composition comprising, consisting of, or consisting essentially of a plant-derived protein source.

DETAILED DESCRIPTION OF THE PREFERRED EMBODIMENT

In one aspect of the present invention, a proteinaceous film-forming composition is provided that, when applied to the exterior surface of comestible particles, provides a protective barrier that renders the particles more resistant to microbial digestion within the forestomach of ruminants, such as cattle or sheep. By applying this technology to vitamins, minerals, proteins, carbohydrates, lipids, antimicrobials, and/or other drug compounds, it is feasible to deliver said compounds intact to the small intestine, thus improving likelihood of adsorption. In so doing, it is possible to improve efficiency of nutrient and/or drug utilization by selecting sites of digestion and adsorption that are more consistent with optimization of animal health and production.

In one embodiment, the protective barrier is created by preparing a solution including 1 to 50% by weight of at least one large, soluble, film-forming biomolecule. The biomolecule preferably comprises a plant-derived protein source, such as a vital wheat gluten, wheat protein isolate, other derivatives of wheat protein, zein protein, and soy protein. As used herein, the term "plant-derived protein source" refers to a concentrated protein product obtained from a plant. Preferably, the plant-derived protein source comprises at least about 50% by weight protein, more preferably at least about 60% by weight, and most preferably at least about 70% by weight. In addition, the protective barrier or film-forming solution comprises less than about 1% by weight of animal protein (such as gelatin or blood meal), and even more preferably is free of any animal protein. The protein source is dissolved in a solute such as water or ethanol. Preferably, the solute comprises from about 50-99% by weight of the solution, more preferably from about 60-95% by weight, and most preferably from about 75-90% by weight. It is important that the protective barrier be substantially insoluble in the rumen of an animal (generally where the pH is greater than about 5) so that digestion of the comestible material coated therewith may occur further down the digestive tract (generally where the pH is less than about 5). Therefore, as preferred protein sources are more soluble in lower pH solutions, acetic acid, hydrochloric acid, or other pH modifiers also may be used with the present invention in order to solubilize the protein source during formation of the protective barrier. The barrier solution generally exhibits a pH of less than about 5, and more preferably between about 2 to about 5.

Optionally, a plasticizer may be added to the film-forming, protective barrier solution in order to improve the rheological properties of the composition. Preferably, the barrier solution comprises from about 0-20% by weight plasticizer, more preferably from about 0.5-15% by weight, and most preferably from about 1-10% by weight. Preferred plasticizers include those selected from the group consisting of glycerol, lactic acid, sorbitol, palmitic acid, stearic acid, and mixtures thereof.

Particulate matter such as vitamins, minerals, amino acids, drugs, nutriceuticals, other food ingredients, or combinations thereof are then added to the barrier solution and blended to form a homogeneous mixture. The particulate matter may be comprised of individual particles or agglomerations of particles. For example, the particulate material may comprise extruded particles, or agglomerations of powders or other particles that have been formed into pellets. The mixture is then dried via vacuum drying, spray-drying, freeze-drying, or even oven-drying to remove excess solute. Preferably, the solute removed from the mixture is captured and reused. Not only does this reuse of solute result in economical savings, but also prevents release of solute into the environment. The resulting dried material comprises the particulate matter encapsulated by a proteinaceous film. The plant derived protein source is preferably the major or predominant constituent of the film. This film, when exposed to the rumen environment, is substantially resistant to microbial degradation, thereby preventing access to the material encapsulated within.

Another aspect of the present invention comprises coating particles to prevent interaction with other components of a mixture. For example, coating of vitamins with a protective barrier may prevent premature oxidation by mineral elements included in the same mixture. Furthermore, in addition to targeted release of encapsulated materials within specific sites of the gastrointestinal tract, the pH-dependent stability of the films may be exploited in food systems, such as with pH-dependent release of reagents in fermented food products.

The protein-based films are also useful as barriers to prevent interactions among ingredients within mixtures, thus preserving their integrity and/or shelf stability. Furthermore, the present invention provides an alternative to current methods for stabilization of vitamins used in humans, ruminants, non-ruminant livestock, aquatic species, and poultry.

The biomolecules, i.e., the proteinaceous film-forming component, may be modified to further improve crosslinking of the protein films. For example, the film-forming component (especially wheat gluten) may be treated with translutainase in order to reduce the susceptibility of the film-forming material to digestion by ruminal microorganisms.

Another aspect of the invention pertains to the encapsulation of selenium, an essential trace element. When fed to ruminant animals such as cattle and sheep, the microorganisms present in the rumen assimilate inorganic forms of selenium (such as sodium selenite or sodium selenite) and produce organic forms of the mineral, including selenomethionine and selenocysteine (selenium-based amino acids). Selenomethionine is considered to have relatively high bioavailability, while selenocysteine is considered to have more limited bioavailability. Sodium selenite and sodium selenate are substantially available for digestion by both ruminant and non-ruminant species. If inorganic forms of selenium are converted to selenocysteine, bioavailability may actually be reduced; consequently, encapsulation improves the overall bioavailability of selenium for ruminants.

The present invention is particularly useful in the encapsulation of vitamins to alter the site of digestion especially in ruminants, to enhance the stability of the vitamins for humans and livestock, to prevent mineral-induced oxidation of other nutrients, and to prevent ruminal microorganisms from converting the encapsulated nutrients from highly available forms to less available forms. A wide variety of materials may be encapsulated so as to alter the site of their digestion in the animal's digestive tract. These materials include fats, amino acids, peptides, proteins, carbohydrates, antimicrobial products, and enzymes. Microorganisms may also be encapsulated to alter the site of colonization or action in the digestive tract. Vaccines may be encapsulated so as to target specific sites of delivery and/or action. Leavening agents or other food additives may be encapsulated so as to promote the timely release of active compounds during selected points of manufacturing, processing, or preparation.

EXAMPLES

The following examples set forth preferred protein-based solutions that, when applied to feed ingredients and dried, will form protective coatings to facilitate altering of the site of digestion in ruminant animals. It is to be understood, however, that these examples are provided by way of illustration and nothing therein should be taken as a limitation upon the overall scope of the invention.

Example 1

This example describes the formation of a film-forming solution for use with the present invention. A film solution is prepared by mixing 18% (w/v) wheat gluten, 85 mL of 95% ethanol, 45 mL of distilled deionized water, and 6.2 g of glycerol in a beaker. The mixture is homogenized and placed onto a heated stir plate for 5 minutes. The acidity of the solution is adjusted to pH 3.3 using glacial acetic acid. The film-forming solution is sheared for 5-10 minutes using a Brink Homogenizer (setting 4). The solution is heated with continuous shearing to a final temperature of 80° C. Finally, the solution is centrifuged at 1000×g for 5 minutes.

Example 2

This example describes the preparation of a film-forming solution in which a simple solvent is used that is readily recovered and re-utilized. Eighteen percent (18%) (w/v) of wheat protein isolate is gradually added to 5% acetic acid during continuous stirring (vortexing) on a low heat setting. The mixture is stirred until completely solubilized.

Example 3

This example describes the preparation of a ruminally protected feed ingredient. Approximately 30% (w/v) of a selected feed ingredient is mixed with a film-forming solution from either of Examples 1 or 2 above. The mixture is thoroughly homogenized and the resulting slurry poured into thin layers on aluminum trays. The trays are placed into a 50° C. oven until dry. Alternatively, the product is spray dried or dried under a vacuum. The resulting product comprises the feed ingredient encapsulated by a thin proteinaceous film that is substantially resistant to ruminal degradation. The film solubilizes when subjected to low pH (approximately 1.5-2) in the abomasum, thereby rendering the encapsulated ingredients available for digestion in the post-ruminal tract.

We claim:

1. An encapsulated comestible material comprising:
   at least one comestible particulate material; and
   a coating composition forming a film and encapsulating said at least one particulate material so as to protect said particulate material against digestion in the rumen of an animal, said coating composition comprising a plant-derived protein source, wherein said protein source is selected from the group consisting of vital wheat gluten, wheat protein isolate, and mixtures thereof, wherein said coating composition is substantially insoluble in the rumen of an animal, wherein said coating composition solubilizes in the abomasum of an animal where the pH is in the range of from 1.5 to 2, thereby rendering said at least one comestible particulate material available for digestion.

2. The encapsulated material of claim 1, wherein said at least one particulate material is selected from the group consisting of vitamins, minerals, amino acids, drugs, food additives, nutriceuticals, microorganisms, enzymes, peptides, proteins, carbohydrates, antimicrobial products, vaccines, and mixtures thereof.

3. The encapsulated material of claim 1, wherein said coating composition comprises from about 1-50% by weight of said protein source.

4. The encapsulated material of claim 1, wherein said coating composition comprises less than 1% by weight animal protein.

5. A method of forming an encapsulated material comprising the steps of:
    providing a film-forming solution comprising a plant-derived protein source selected from the group consisting of vital wheat gluten, wheat protein isolate, and mixtures thereof, wherein said film-forming solution has a pH of less than 5;
    coating at least one particulate comestible material with said film-forming solution; and
    drying said film-forming solution on said at least one particulate comestible material thereby forming said encapsulated material by forming a film around and encapsulating said at least one particulate comestible material so as to protect said particulate material against digestion in the rumen of an animal,
    wherein said film solubilizes in the abomasum of an animal where the pH is in the range of from 1.5 to 2, thereby rendering said at least one comestible particulate material available for digestion.

6. The method of claim 5, wherein said at least one comestible material is selected from the group consisting of vitamins, minerals, amino acids, drugs, food additives, nutriceuticals, microorganisms, enzymes, peptides, proteins, carbohydrates, antimicrobial products, vaccines, and mixtures thereof.

7. The method of claim 5, wherein said film-forming solution comprises from about 1-50% by weight of said protein source.

8. The method of claim 5 wherein said film-forming solution comprises less than 1% by weight animal protein.

9. The method of claim 5, wherein said film-forming solution comprises a solute selected from the group consisting of water, ethanol, acetic acid, hydrochloric acid, and mixtures thereof.

10. The method of claim 5, wherein said coating step comprises blending said particulate comestible material and said film-forming solution to form a homogeneous mixture.

11. The method of claim 5, wherein said drying step comprises vacuum drying, spray-drying, freeze-drying, oven-drying, or a combination thereof.

12. A method of feeding an animal or a human comprising:
    feeding said animal or human the encapsulated particulate material according to claim 1.

13. The method of claim 12, wherein said particulate material is selected from the group consisting of vitamins, minerals, amino acids, drugs, food additives, nutriceuticals, microorganisms, enzymes, peptides, proteins, carbohydrates, antimicrobial products, vaccines, and mixtures thereof.

14. The method of claim 12, wherein said film-forming composition comprises less than 1% by weight animal protein.

15. The method of claim 12, wherein said animal is a ruminant animal.

16. An encapsulated comestible material comprising:
    at least one comestible particulate material consisting essentially of one or more members selected from the group consisting of vitamins, minerals, amino acids, drugs, microorganisms, enzymes, and vaccines; and
    a coating composition forming a film and encapsulating said at least one particulate material so as to protect said particulate material against digestion in the rumen of an animal, said coating composition comprising a plant-derived protein source,
    wherein said protein source is selected from the group consisting of vital wheat gluten, wheat protein isolate, and mixtures thereof,
    wherein said coating composition is substantially insoluble in the rumen of an animal,
    wherein said coating composition solubilizes in the abomasum of an animal, where the pH is in the range of from 1.5 to 2, thereby rendering said at least one comestible particulate material available for digestion.

* * * * *